United States Patent
Hunter (10) Patent No.: US 10,030,639 B2
(45) Date of Patent: Jul. 24, 2018

(54) PRESSURE INTENSIFICATION DEVICE

(71) Applicant: Junius Hunter, Nashville, TN (US)

(72) Inventor: Junius Hunter, Nashville, TN (US)

( * ) Notice: Subject to any disclaimer, the term of this patent is extended or adjusted under 35 U.S.C. 154(b) by 354 days.

(21) Appl. No.: 14/779,891

(22) PCT Filed: Mar. 25, 2014

(86) PCT No.: PCT/US2014/031762
§ 371 (c)(1),
(2) Date: Sep. 24, 2015

(87) PCT Pub. No.: WO2014/160727
PCT Pub. Date: Oct. 2, 2014

(65) Prior Publication Data
US 2016/0053749 A1  Feb. 25, 2016

Related U.S. Application Data (60) Provisional application No. 61/852,873, filed on Mar. 25, 2013.

(51) Int. Cl.
| | |
|---|---|
| *F04B 3/00* | (2006.01) |
| *F15B 3/00* | (2006.01) |
| *F04B 9/109* | (2006.01) |
| *F04B 9/113* | (2006.01) |
| *A61M 5/142* | (2006.01) |

(52) U.S. Cl.
CPC ........... *F04B 3/00* (2013.01); *A61M 5/14216* (2013.01); *F04B 9/109* (2013.01); *F04B 9/113* (2013.01); *F15B 3/00* (2013.01)

(58) Field of Classification Search
CPC .. F04B 3/00; F04B 9/109; F04B 9/113; F04B 53/14; F04B 53/148; F15B 3/00
USPC ................................. 417/225, 226, 534–537
See application file for complete search history.

(56) References Cited

U.S. PATENT DOCUMENTS

| | | | |
|---|---|---|---|
| 702,430 A | 6/1902 | Hobart | |
| 4,512,151 A | 4/1985 | Yamatani | |
| 4,627,794 A * | 12/1986 | Silva | F04B 9/115 417/225 |
| 5,065,607 A | 11/1991 | Kadis et al. | |
| 5,560,456 A | 10/1996 | Koch | |
| 7,469,664 B2 | 12/2008 | Hofbauer | |

* cited by examiner

*Primary Examiner* — Kenneth J Hansen
(74) *Attorney, Agent, or Firm* — Stites & Harbison PLLC; Richard S. Myers, Jr.

(57) ABSTRACT

The presently-disclosed subject matter includes a pressure intensification device that increases the pressure of a fluid at a first pressure to a second higher pressure. In some embodiments the devices comprises an outer shell, and outer element housed within the outer shell, and an inner element housed within the outer element, the inner and outer elements being configured to slide in a reciprocating manner within the outer shell to increase the pressure of a fluid. In some embodiments the device does not comprise an additional power source or motor to increase the pressure of the fluid to a second pressure.

39 Claims, 6 Drawing Sheets

PRESSURE INTENSIFICATION DEVICE

RELATED APPLICATION

This application claims priority from U.S. Provisional Patent Application No. 61/852,873, filed Mar. 25, 2013, the entire disclosure of which is incorporated herein by this reference.

TECHNICAL FIELD

The presently-disclosed subject matter relates to a pressure intensification device. In particular, the presently-disclosed subject matter relates to a device that can increase the pressure of a pressurized fluid without any additional power source as well as methods thereof.

INTRODUCTION

Fluids pressurized by various different means are used for a multitude of purposes. For example, water is often pressurized for spraying, cleaning, water jet milling, and the like. Indeed, pressure washers and the like are used for both personal and commercial applications to scrape, polish, or otherwise clean surfaces with pressurized water.

Current devices and methods for pressuring fluids comprise a pump that can subject the fluid to an increased pressure. Displacement pumps, such as rotary, reciprocating, or screw pumps, can all pressurize a fluid. Centrifugal pumps and the like can also pressurize fluids and may be desirable in certain applications. Known pumps are typically operated by a motor that is itself powered by an electrical or fuel source.

Known fluid pressurization devices therefore rely on integral or auxiliary motors in order power a pump that pressurizes the fluid. Such motors can include battery powered electric motors, alternating current powered motors, gas powered motors, or the like. However, the requirement for a motor and/or power source can make pressurization devices large and difficult to operate. Gas motors in particular can be loud and unpleasant to operate. Motors in pressurizing devices also represent an additional cost both to the manufacturer who has to incorporate a motor into a device as well as the consumer who has to supply electricity or fuel to the motor.

Hence, there remains a need for fluid pressurization devices that do not require a motor to pressurize a fluid. There also remains a need for fluid pressurization devices that are simple, cost-effective, and efficient to operate.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a device that can receive a fluid at a first pressure and release it at a second pressure, the second pressuring being greater than the first pressure. In some embodiments the devices include an outer shell that includes a center section positioned between a first distal section and a second distal section, a driving chamber defined by the center section, an inlet in communication with the driving chamber, an annular outer element housed within the outer shell including a first outer piston that is coupled to and opposed to a second outer piston, each of the outer pistons forming a seal with an interior side of the outer shell and being slideably received by the respective distal sections, an inner element housed within the outer element including a first inner piston that is coupled to and opposed to a second inner piston, each of the inner pistons being slideably received by and being configured to form a seal with the respective outer pistons, a first pressurization chamber within the first distal section that includes a first outlet and a second pressurization chamber within the second distal section that includes a second outlet, the pressurization chambers being defined by interior sides the respective distal sections, a distal end of the respective outer pistons, and a distal end of the respective inner pistons, and a first channel communicating between the driving chamber and the first pressurization chamber and a second channel communicating between the driving chamber and the second pressurization chamber. The device can further comprise a device outlet in communication with the first outlet, the second outlet, or both.

In some embodiments each of the outer pistons include an outer piston head and an outer piston body distally extending from the respective outer piston heads, each of the outer piston heads forming a seal with the interior side of the driving chamber, and each of the outer piston bodies being slideably received by and forming a seal with the respective distal sections. A diameter of the outer piston head can be greater than a diameter of the outer piston body.

Alternatively or additionally, in some embodiments each of the inner pistons include an inner piston head and an inner piston body distally extending from the respective inner piston heads, each of the inner piston heads being configured to form a seal with the outer piston heads, and each of the inner piston bodies being slideably received by and being configured to form a seal with the respective outer pistons and/or outer piston bodies. A diameter of the inner piston head can be greater than a diameter of the inner piston body. In certain embodiments the outer piston heads each comprise a seat for engaging the respective inner piston heads.

In some embodiments of the present device the first channel can be closed at least when the first inner piston is fully received by the second outer piston, and the second channel can be closed at least when the second inner piston is fully received by the second outer piston.

In some embodiments the device can further comprise a first stop post and a second stop post housed within the respective pressurization chambers, the stop posts being configured to limit the range of motion of the inner element with respect to the outer element. In exemplary devices the first stop post can be configured open the first channel when the first outer piston is fully received by the first pressurization chamber, the second stop post can be configured open the second channel when the second outer piston is fully received by the second pressurization chamber, or both.

In some embodiments the outer element and the inner element are configured to slide in a reciprocating manner within the outer shell.

In some embodiments one or both of the first high pressure outlet and the second high pressure outlet include a valve.

Some embodiments of the present device can further comprise a loop channel in communication with the first outlet and the second outlet.

In some embodiments one or more of the seals include an o-ring.

In some embodiments the device does not comprise an additional power source.

In some embodiments the first outer piston and the second outer piston are coupled via a fluid permeable structure. For example, the fluid permeable structure can include a plurality of bolts coupling the first outer piston to the second outer piston.

In some embodiments the first channel is positioned between the first inner piston and the first outer piston, the second channel is positioned between the second inner piston and the second outer piston, or both. Furthermore, in some embodiments the device comprises a first protrusion extending from the distal end of the first inner piston for engaging the first stop post, a second protrusion extending from the distal end of the second inner piston for engaging the second stop post, or both.

Some embodiments of the present device can further comprise a first outer sleeve positioned in the first pressurization chamber for receiving the first outer piston, a second outer sleeve positioned in the second pressurization chamber for receiving the second outer piston, or both.

The presently-disclosed subject matter further includes a device for increasing the pressure of a fluid that comprises an outer shell that includes a center section positioned between a first distal section and a second distal section, a driving chamber defined by the center section, an inlet in communication with the driving chamber, an annular outer element housed within the outer shell including a first outer piston that is coupled to a second outer piston, each outer piston including an outer piston head that forms a seal with an interior side of the center section and an outer piston body that extends from each of the respective outer piston heads, the outer piston bodies being slideably received by and forming a seal with the respective distal sections, an inner element housed within the outer element including a first inner piston that is coupled to a second inner piston, each of the inner pistons including an inner piston head that is configured to form a seal with the respective outer pistons and an inner piston body that extends from each of the respective inner piston heads, the inner piston bodies being slideably received by and forming a seal with the respective outer piston bodies, a first pressurization chamber that includes a first outlet and a second pressurization chamber that includes a second outlet, the pressurization chambers being defined by the respective distal sections, a distal end of the respective outer pistons, and a distal end of the respective inner pistons, a first channel communicating between the driving chamber and the first pressurization chamber and a second channel communicating between the driving chamber and the second pressurization chamber, and a device outlet in communication with the first outlet, the second outlet, or both.

The presently-disclosed subject matter further includes methods for increasing the pressure of a fluid. In one embodiment a method comprises providing a device that includes an outer shell that includes a center section positioned between a first distal section and a second distal section, a driving chamber defined by the center section, an inlet in communication with the driving chamber, an annular outer element housed within the outer shell including a first outer piston that is coupled to and opposed to a second outer piston, each of the outer pistons forming a seal with an interior side of the outer shell and being slideably received by the respective distal sections, an inner element housed within the outer element including a first inner piston that is coupled to and opposed to a second inner piston, each of the inner pistons being slideably received by and being configured to form a seal with the respective outer pistons, a first pressurization chamber within the first distal section that includes a first outlet and a second pressurization chamber within the second distal section that includes a second outlet, the pressurization chambers being defined by interior sides the respective distal sections, a distal end of the respective outer pistons, and a distal end of the respective inner pistons, a first channel communicating between the driving chamber and the first pressurization chamber and a second channel communicating between the driving chamber and the second pressurization chamber, and a device outlet in communication with the first outlet, the second outlet, or both. The method can further comprise providing a fluid at a first pressure to the device inlet, and then releasing the fluid at a second pressure via the device outlet, the second pressure being greater than the first pressure. The fluid can include water.

In some embodiments a ratio of the second pressure to the first pressure is about 2 to about 30. For example, in some embodiments the first pressure is about 20 psi to about 5,000 psi and the second pressure is about 50 psi to about 100,000 psi. The present methods can include utilizing the fluid at the second pressure for a cleaning process, a milling process, or a combination thereof.

DESCRIPTION OF EXEMPLARY EMBODIMENTS

The details of one or more embodiments of the presently-disclosed subject matter are set forth in this document.

Modifications to embodiments described in this document, and other embodiments, will be evident to those of ordinary skill in the art after a study of the information provided in this document. The information provided in this document, and particularly the specific details of the described exemplary embodiment, is provided primarily for clearness of understanding and no unnecessary limitations are to be understood therefrom. In case of conflict, the specification of this document, including definitions, will control.

The presently-disclosed subject matter includes a pressure intensification device. Exemplary pressure intensification devices can receive a fluid at a first pressure and release the fluid at a second pressure. In some instances the fluid includes water. The present devices can be provided to, among other things, provide pressurized fluid for cleaning processes, milling processes, or the like. In some embodiments the devices do not comprise an additional power supply and/or motor, and can operate by only utilizing a fluid at a first pressure to increase the pressure of the fluid to a higher second pressure.

Figure 1:
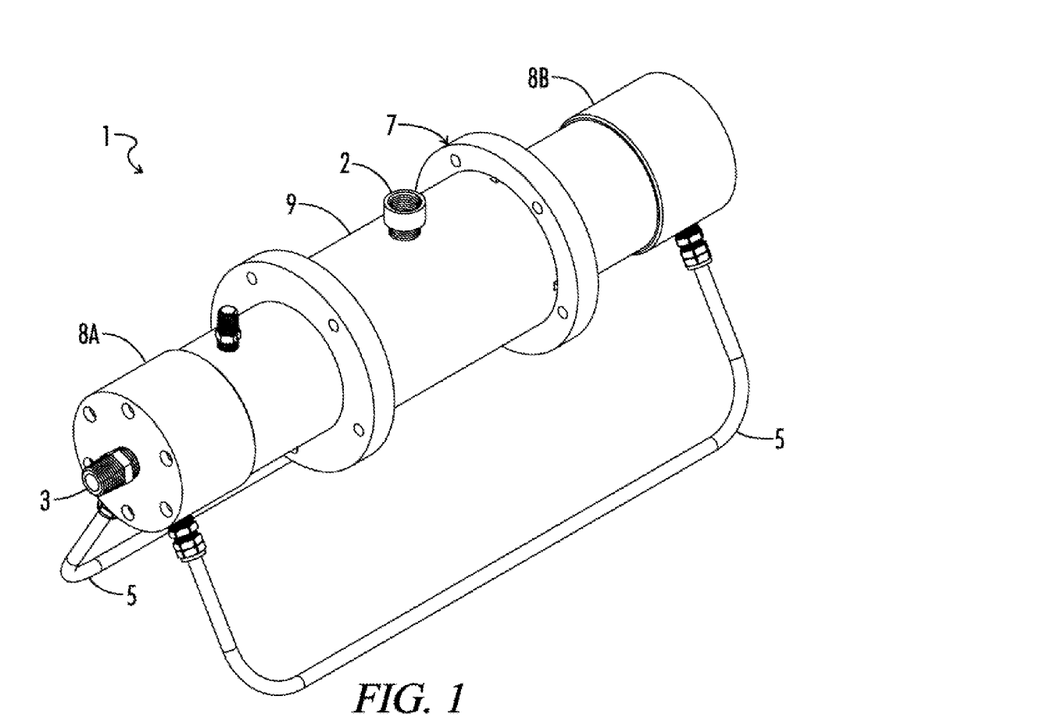
FIG. 1 shows a prospective view of an embodiment of a pressure intensification device.

Turning now to the Figures, various views of an embodiment of a pressure intensification device are shown. FIG. 1 shows a prospective view of a pressure intensification device 1. The device 1 includes an outer shell 7 substantially forming the outer body of the device 1. The outer shell 7 is substantially divided into a center section 9, a first distal section 8A, and a second distal section 8B. The center section 9 is position between the first distal section 8A and the second distal section 8B.

In this regard, the term "distal" as used herein with respect to the present device refers to a direction that generally points towards the opposing ends of the device as viewed in the Figures, and does not necessarily imply a point at the extreme end of an object. Thus, the term distal is inclusive of "being distal relative to," and the like. On the other hand, the term "central" refers to a direction that generally points toward the middle of the device depicted in the Figures. Furthermore, embodiments of the present device can also comprise a plurality of certain elements, and such elements are referred to as a first element (labeled as 'A') and a second element (labeled as 'B'). For example, a device can comprise a first outer piston 20A and a second outer piston 20B. For the purposes of this description only, a first element and a second element generally refer to an element on, respectively, a left hand side and a right hand side of the device as seen in the Figures.

FIG. 1 shows that the outer shell 7 includes a generally cylindrical shape, although the device 1 and the outer shell 7 can comprise a different exterior shape in certain instances. The center section 9 of the outer shell 7 is formed from one cylindrically shaped object, and the distal sections 8 are each formed from two attached cylindrically shaped objects. In other embodiments each section can comprise any number of distinct objects that are connected to form one section. In yet other embodiments any combination of the center section, the first distal section, and the second distal section can be formed from one continuous object. Also shown is an inlet 2 positioned on the center section 9, a device outlet 3 positioned on the distal end of the first distal section 8A, and loop channels 5 extending between the first distal end to the second distal end.

Figure 2:
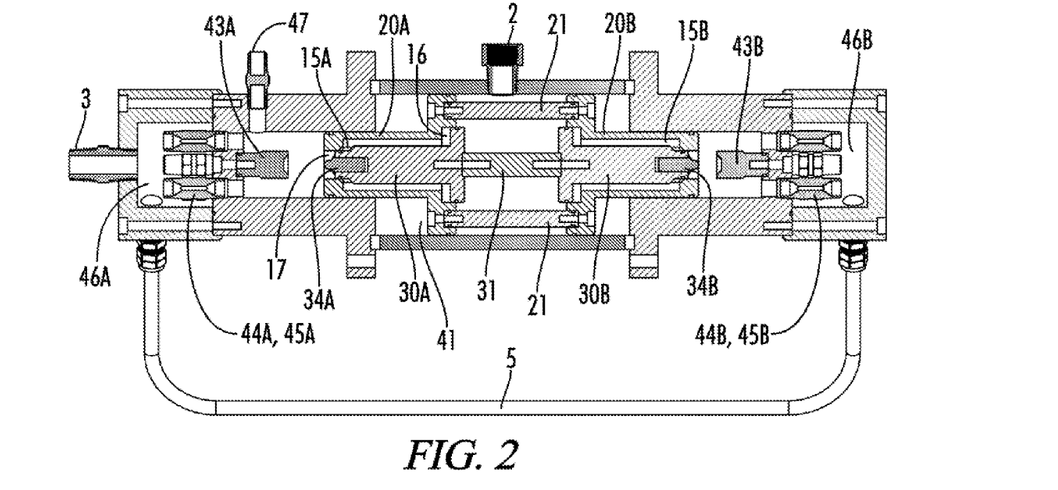
FIG. 2 shows a cross sectional view of the embodied pressure intensification device.

FIG. 2 shows a cross sectional view of the exemplary fluid pressure intensification device 1. FIG. 2 shows the profile and the interior sides of the first distal section 8A, the center section 9, and the second distal section 8B of the outer shell 7. The center section 9 defines a driving chamber 41. More specifically, the interior side of the center sections 9 and central ends of the distal sections 8 define the driving chamber 41. The inlet 2 provided on the center section 9 is in communication with the driving chamber 41. The inlet 2 can be provided on other locations of the device 1 so long as it communicates with the driving chamber 41 and can deliver a fluid thereto.

The device 1 also includes an outer element 13 that is housed within the outer shell 7. The outer element 13 is cylindrical and annular, thereby providing an opening that extends the longitudinal length of the outer element 13. The outer element 13 includes a first outer piston 20A that is coupled to a second outer piston 20B via an outer piston connector 21. The first outer piston 20A and the second outer piston 20B can be coupled so that they are facing opposite directions (i.e., are opposed to one another). Furthermore, each of the outer pistons 20 can form a seal 50 with an interior side of the outer shell 7. When referring to any seals herein, such seals can be o-rings in some embodiments, including rubber or polymer o-rings. For instance, each outer piston 20 can include an o-ring around its exterior side that forms a seal 50 with an interior side of the outer shell 7. The outer pistons 20 can each also be slideably received by the respective distal sections 8 (i.e., first outer piston 20A received by first distal section 8A, second outer piston 20B received by second distal section 8B).

In the illustrated embodiment, each outer piston 20 includes an outer piston head 25 located at a central end of the outer pistons 20 as well as an outer piston body 23 distally extending from the respective outer piston heads 25. The outer piston heads 25 are dimensioned such that they can be located and move in a reciprocating manner with respect to the driving chamber 41. The outer piston heads 25 generally comprise a portion of the outer pistons 20 that have a larger diameter relative to the rest of the outer piston 20 and are dimensioned to move within the driving chamber 41. The outer piston bodies 23 are dimensioned such that they can be slideably received by the distal sections 8 of the outer shell 7. The embodied outer pistons 20 each form two seals 50 with the interior side of the outer shell 7. The outer piston heads 25 each form a seal 50 with an interior side of the driving chamber 41. The outer piston bodies 23 each form a seal 50 with the interior side of the distal sections 8, and, in the present embodiment, the seal 50 is positioned at or in proximity to the distal end of outer piston bodies 23. The diameter of the outer piston head 25 can be greater than a diameter of the outer piston body 25.

The outer pistons 20 can be coupled to one another via a fluid permeable structure. For instance, the outer pistons 20 can be coupled with bolts, a mesh-like object, or another structure that permits fluid to flow therethrough. In this manner, when a fluid is introduced into the driving chamber 41 via the inlet 2 at a location between the two outer pistons 20, the fluid can flow through the fluid permeable structure to reach the interior side of the outer element 13.

The device 1 also includes an inner element 11 that is wholly or substantially housed within the outer element 13. In some instances, for example, the distal ends of the inner element 11 may protrude from the outer element 13, yet the inner element 11 is substantially housed within the outer element 13. The inner element 11 can be cylindrical. The inner element 11 can include a first inner piston 30A that is coupled via an inner piston connector 31 to a second inner piston 30B. The first inner piston 30A and the second inner piston 30B can be coupled so that they are facing opposite directions or are opposed to one another. Furthermore, each of the inner pistons 30 can be configured to form a seal 50 with an interior side of the respective outer pistons 20. For instance, each inner piston 30 can include an o-ring around its exterior side that forms a seal 50 with an interior side of a respective outer piston 20. The inner pistons 30 can also each be slideably received by the respective outer pistons 20.

In the illustrated embodiment, each inner piston 30 includes an inner piston head 35 located at a central end of the inner pistons 30 as well as an inner piston body 33 distally extending from the respective inner piston heads 35. The inner element 11 is located in and is dimensioned such that it can move in a reciprocating manner within the outer element 13. The inner piston bodies 33 are dimensioned such that they can be slideably received by the outer pistons 20, including the outer piston bodies 23. The embodied inner pistons 30 can be each configured to form two seals 50 with the interior side of the outer pistons 20. The seals 50 can be formed or opened depending on the position of the inner element 11 relative to the outer element 13.

For instance, looking to FIG. 2, the inner piston heads 35 are each configured to form a seal 50 with the respective outer pistons 20, and in some instances the respective outer piston heads 25. In the present embodiment each of the outer piston heads 25 comprise a seat 27 on a central side thereof configured to engage the inner piston heads 35. The seat 27 can be a cavity that corresponds in shape and size to the inner piston heads 35. In this manner, a seal 50 can be formed when the inner piston heads 35 engage the respective seats 27 of the outer pistons 20. Additionally, the inner piston bodies 33 can each be configured to form a seal 50 with interior sides of the outer pistons 20, and in some instances the interior sides of the outer piston bodies 23. In some embodiments the seal 50 of the inner piston bodies 33 are positioned at or are in proximity to the distal end of inner piston bodies 33. The diameter of the inner piston head 35 can be greater a diameter of the inner piston body 33.

FIG. 2 further shows that the first distal section 8A includes a first pressurization chamber 42A and the second distal section 8B includes a second pressurization chamber 42B. While a pressure within the pressurization chambers 42 can be greater than a pressure within the driving chamber 41, this is not necessarily the case in all embodiments or at all times. Each of the respective pressurization chambers 42 are defined by an interior side of the respective distal sections 8, a distal end of the respective outer pistons 20, and a distal end of the respective inner pistons 30.

Each pressurization chamber 42 also comprises a stop post 43. The stop posts 43 are a generally protruding object and are positioned at the center of a distal wall of the pressurization chamber 42. In this manner, the stop posts 43 can be configured to limit the range of motion of the inner element 11 with respect to the outer element 13. In other words, the stop posts 43 can be positioned and dimensioned such that they contact and limit the range of motion of the inner element 11, but can still permit the outer element 13 to move beyond the stop post 43. As shown in FIG. 2, the stop posts 43 can be cylindrically shaped protrusions dimensioned to contact the inner element 11, but can be small enough so that they can extend within the interior sides of the outer pistons 20 and/or the outer piston bodies 23.

One or both of the pressurization chambers 42 can further include an outlet 44 to release a fluid from the pressurization chamber 42. The outlet 44 communicates between the respective pressurization chambers 42 and respective exit chambers 46. One or both of the outlets 44 can include a valve 45 (e.g. check valve). The valve 45 can be set a second pressure that is higher than a first pressure of the fluid being delivered to the device inlet 2.

The present device can be further provided with outer sleeves. The outer sleeves are positioned in the respected pressurization chambers 42 and are for receiving the respective outer pistons. Thus, the outer sleeves can be annular, cylindrical sleeves that are configured to line an interior side of the pressurization chambers 42. Embodiments of devices can comprise an outer sleeve in one or both pressurization chambers 42. In some embodiments an outer sleeve can made of a material that is more resistant to corrosion and/or forms a superior seal with the outer piston relative to a material of the distal section 8. In other embodiments the outer sleeves are replaceable and provide a relatively easy method for repairing portions of the device that are subjected to frictional or corrosive forces.

The embodied device 1 can also include one or more loop channels 5 that are in communication with the first outlet 44A of the first pressurization chamber 42A and the second outlet 44B of the second pressurization chamber 42B. The depicted loop channel 5 is in communication with a first exit chamber 46A and a second exit chamber 46B. The loop channel 5 can be a pipe or the like. In different embodiments the loop channel(s) 5 are external to the outer shell 7, completely housed within the outer shell 7, or a combination thereof. Exemplary loop channels 5 can be provided to unify the fluid streams from the first outlet 44A and the second outlet 44B, to equalize pressures of the fluid released from the first outlet 44A and the second outlet 44B, or the like. The loop channel 5 can be directly coupled to the outlets 44 of the pressurization chambers 42 and/or can be coupled to exit chambers 46, which can serve as temporary holding areas for the fluid before it is released from the device 1. In other embodiments one or both outlets 44 of the pressurization chambers 42 can release a fluid directly from the device 1 and/or are not in communication with one another.

In this regard, the device 1 also comprises a device outlet 3 that is in communication with the first outlet 44A and the second outlet 44B, and fluid released from the first and second outlets 44 can be released via the device outlet 3 positioned on the first exit chamber 46A. If no exit chambers 46 are provided, the pressurization chamber outlets 44 can themselves be device outlets 3. Furthermore, the device outlet 3 need not be provided only on the first exit chamber 46A, but can instead be provided on the second exit chamber 46B, on both exit chambers 46, on the loop channel 5, or at any other position so long as it is in communication with at least one of the pressurization chamber outlets 44.

The present device 1 further includes a first channel 15A communicating between the driving chamber 41 and the first pressurization chamber 42A and a second channel 15B communicating between the driving chamber 41 and the second pressurization chamber 42B. The channels 15 can be configured such that the first channel 15A is closed at least when the first inner piston 30A is fully received by the first outer piston 20A, and the second channel 15B is closed at least when the second inner piston 30B is fully received by the second outer piston 20B. Fully received refers to a point at which the inner piston cannot extend further into the outer piston, or the like. In the present device 1, when the first channel 15A is completely opened the second channel 15B is completely closed, and vice versa.

In this regard, in the present device 1 the stop posts 43 provided in the pressurization chambers 42 can drive the opening and closing of the respective channels 15. For instance, when the first outer piston 20A is fully received by the first pressurization chamber 42A the stop post 43A can block the inner piston 30A in a lesser extended position relative to the outer piston 20A, thereby opening the pressurization chamber side opening (channel outlet 17) and the driving chamber side opening (channel inlet 16) of the first channel 15A. The channel openings can be referred to as a channel outlet 17 and a channel inlet 16 herein since, as described further below, the openings can generally function as such when the device 1 is being operated.

Figure 3:
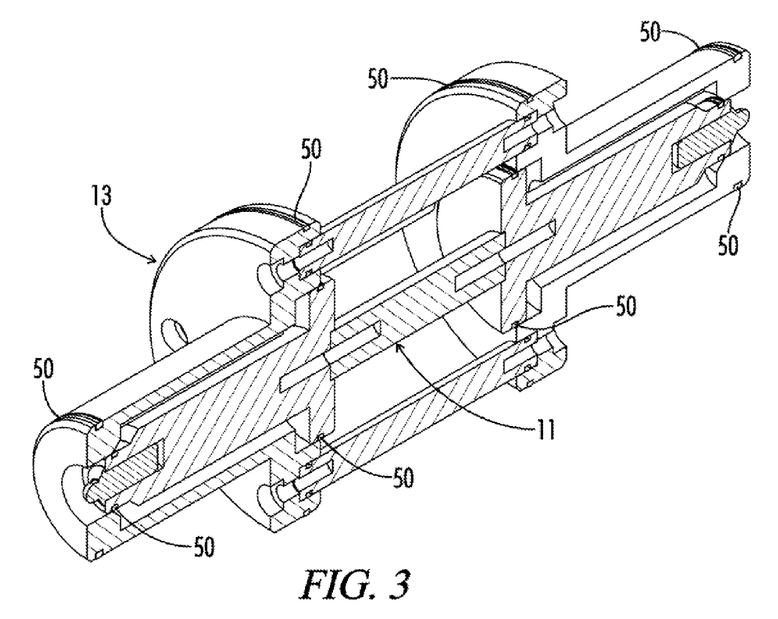
FIG. 3 shows a cross sectional view of the outer element and the inner element of the embodied pressure intensification device.

Looking now to FIG. 3, a cross sectional view of the inner element 11 and the outer element 13 is shown. FIG. 3 shows that protrusions 34 can be provided on the distal ends of the inner pistons 30. The protrusions 34 can contact the stop posts 43 during operation. In some embodiments the protrusions 34 are spring-loaded, and in certain embodiments the protrusions 34 include spring plungers.

FIG. 3 also shows that the first channel 15A is open and is positioned between the first inner piston 30A and the first outer piston 20A, whereas the second channel 15B is closed and is positioned between the second inner piston 30B and the second outer piston 20B. The seal 50 between the first inner piston 30A and the second outer piston 20B is broken when the first inner piston head 35A disengages the first outer piston 20A, thereby providing an opening for a fluid to communicate with a first channel inlet 16A. A channel outlet 17 is provided at a distal end of the interior side of the outer pistons 20. In this manner, when either of the inner pistons 30 disengage the respective outer pistons 20, the respective channel outlets 17 are opened and permit fluid to release from distal ends of the respective outer pistons 20.

Figure 4:
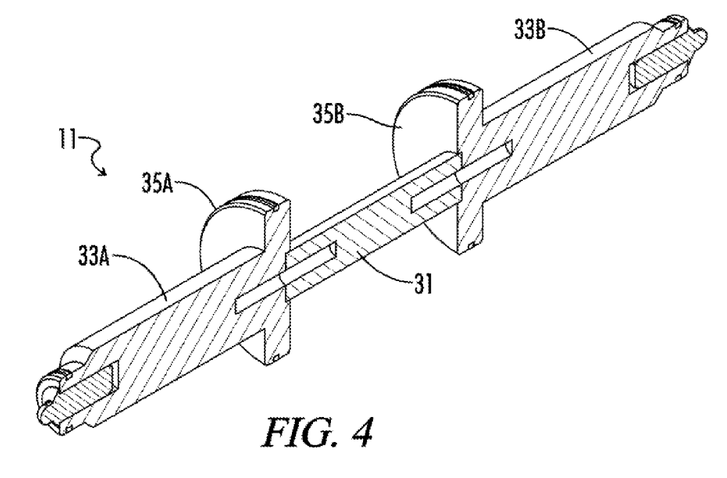
FIG. 4 shows a cross sectional view of the inner element of the embodied pressure intensification device.
Figure 5:
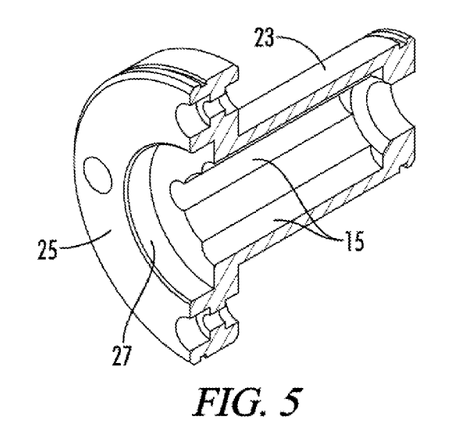
FIG. 5 shows a cross sectional view of the outer piston of the embodied pressure intensification device.

FIG. 4 shows the inner element 11 only, and shows that the inner element 11 can comprise a pair of seals 50 that can seal to the interior side of the outer piston in order to close the first and second channels 15B. More specifically, FIG. 5 shows a cross sectional view of an outer piston 20 that comprises a plurality of grooves on the interior side of the outer piston body 23 extending along the longitudinal length of the outer piston 20. The first channel 15A and the second channel 15B are comprised of these grooves. The channels 15 are open when a fluid can pass between outer piston 20 and the inner piston 30 through the grooves (channels), which occurs when the seals 50 of the inner piston 30 disengage the interior side of the outer piston 20. FIG. 5 also shows an optional seat 27 on a central side of the outer piston head 25 that is configured to receive an inner piston head 35. The seat 27 can allow the inner piston head 35 and the outer piston head 25 to form a seal and also to form a substantially flat surface for fluid compression, as discussed further below.

In other embodiments the device can further include inner sleeves. Similar to the outer sleeves, the inner sleeves can line interior sides of the outer pistons 20, including interior sides of the outer piston bodies 23. Inner sleeves can provide higher corrosion resistance, better tolerances, and enhanced methods for repairing the device. The first and second channels 15 can be provided in the first and second inner sleeves, respectively. In some instances the channels 15 are located between the inner sleeve and the outer pistons 20.

The present pressure intensification device can provide numerous benefits over other known pressure intensification devices. Embodiments of the device do not require auxiliary power or motors to drive a pump, and therefore the device can have a lower manufacturing cost, operational cost, or both. The absence of a motor can make operation of the device quieter, easier, and safer.

The configuration of the described embodiment can also be beneficial. For instance, the embodiment described herein has opposing pistons, and the opposing nature of the pistons can make operation of the device more efficient. The opposing pistons or the characteristic of having two pressurization chambers can also provide a more stable stream of pressurized fluid, since fluid is pressurized during both strokes of the pistons in either the first pressurization chamber or the second pressurization chamber. This is in contrast to the device shown in U.S. Pat. No. 6,857,158, which is incorporated herein by this reference.

Referring now to FIGS. 2 and 6 to 11, views of the device 1 at various stages of operation are shown to illustrate the mechanism of the device 1. During operation a fluid (e.g., water) is supplied to the device inlet 2 at a first pressure (e.g., 20 psi to 5,000 psi). In FIG. 2 the inner element 11 is in the full right position relative to the outer element 13, and therefore the second inner piston 30B is sealed inside the second outer piston 20B with two o-rings. This creates a device 1 for compressing fluid in the second pressurization chamber 42A.

In some embodiments operation of the device 1 is commenced by initially introducing some or all of the fluid to the device 1 via a input valve 47 or input check valve that is in communication with one or both of the pressurization chambers 42. In the present embodiment the input valve 47 is in communication with the first pressurization chamber 42A. As the fluid enters into the first pressurization chamber 42A via the input valve 47, the fluid creates a flow bias in the device 1 such that the inner element 11 and the outer element 13 are pushed to the right.

Regardless of whether the device 1 comprises an input valve 47, as fluid at a first pressure enters the driving chamber 41, the now combined piston assembly is pushed to the right, compressing the fluid in the second pressurization chamber 42B by hydraulic intensification. While the combined piston assembly is moving right, the first channel 15A in the left half is open, allowing fluid to flow through and replenish the first pressurization chamber 42A.

To maintain pressurized fluid in the driving chamber 41, check valves 45 of the pressurization chamber outlets 44 are set to a second cracking pressure that is higher than the first pressure. This prevents the supplied fluid at a first pressure from exiting through the pressurization chamber 42 at the opposite end of the device 1 while it is being replenished through its channels 15. When fluid in the second pressurization chamber 42B is compressed at or above the second pressure rating for the check valves 45, fluid will flow through the check valves 45 in the second pressurization chamber 42B and exit through the second outlet 44B.

The degree of pressurization can depend on a ratio (pressurization ratio) of the cross sectional areas of the inner piston heads and the outer piston heads to the cross sectional areas of the distal ends of the inner pistons 30 and the outer pistons 20 (i.e., cross sectional area of driving chamber 41 to the cross sectional area of the pressurization chambers 42). In some embodiments the pressurization ratio can be about 2, 3, 4, 5, 6, 7, 8, 9, 10, 11, 12, 13, 14, 15, 16, 17, 18, 19, 20, 21, 22, 23, 24, 25, 26, 27, 28, 29, 30, or more, and can correlate with the degree of pressurization. Thus, a device with a pressurization ratio of 2 can intensify the pressure of a fluid by a factor of about 2. This hydraulic advantage is created by the ratio difference between the combined driving chamber 41 side piston face areas and the combined pressurization chamber 42 side piston face areas.

Furthermore, in some embodiments the inner pistons and/or inner piston heads have a greater compression ratio than the outer pistons and/or outer piston heads. In some instances having an inner piston with a greater compression ratio (i.e., surface area for compression or inner piston head surface area) can permit the inner pistons to seat and seal with the outer piston, since the force of the pressurized fluid on the inner piston 30 will be greater than the force of the pressurized fluid on the outer piston.

In this regard, in some embodiments the fluid supplied to the device is at a first pressure of about 20, 30, 40, 50, 60, 70, 80, 90, or 100 psi. The first pressure can also be about 100, 200, 300, 400, 500, 600, 700, 800, 900, 1,000, 2,000, 3,000, 4,000, or 5,000 psi. In some embodiment the fluid released from the device is at a second pressure of about 50, 100, 150, 200, 250, 300, 400, 500, 600, 700, 800, 900, or 1,000 psi. The second pressure can also be about 2,000, 5,000, 10,000, 20,000, 30,000, 40,000, 50,000, 60,000, 70,000, 80,000, 90,000, or 100,000 psi.

Figure 6:
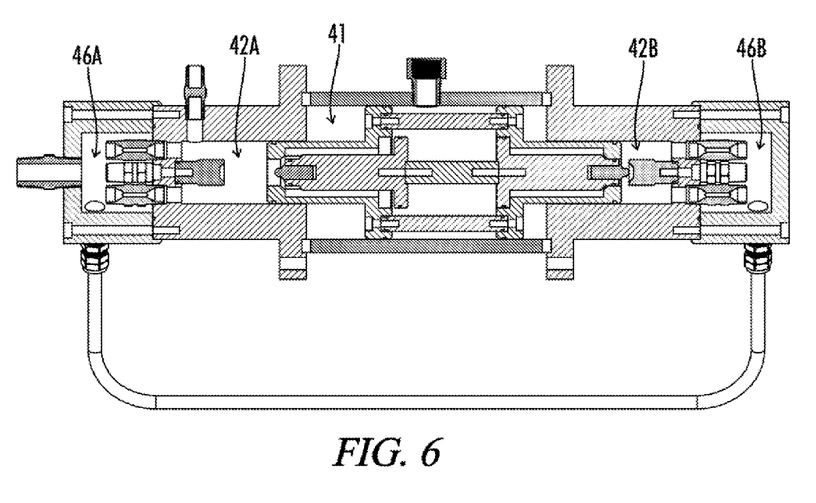
FIG. 6 shows a cross sectional view of the embodied pressure intensification device.

Looking now to FIG. 6, as the combined inner and outer elements 11, 13 are pushed right from an influx of fluid at a first pressure in the driving chamber 41, the second inner piston 30B encounters the second stop post 43B in the center of the second pressurization chamber 42B, thereby stopping the inner element 11 from moving to the right. When the second inner piston 30B first contacts the second stop post 43B the seals 50 between the second outer piston 20B and the second inner piston 30B are still closed.

Figure 7:
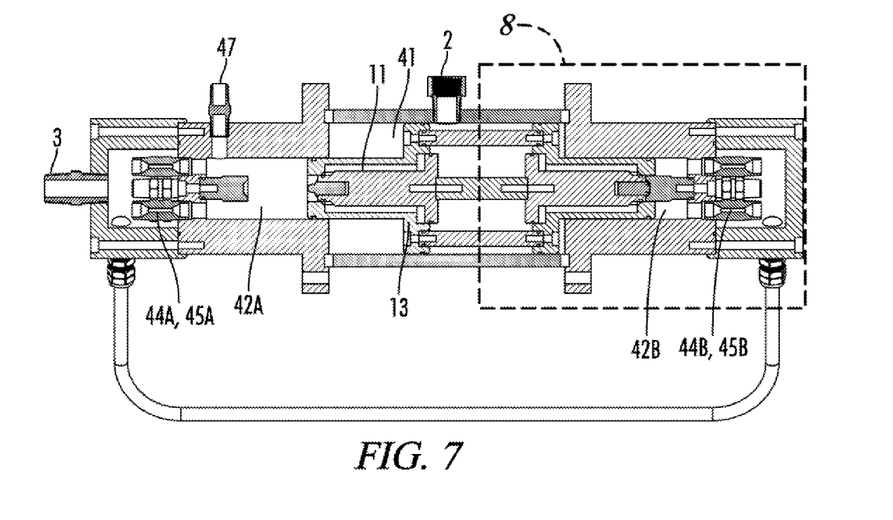
FIG. 7 shows a cross sectional view of the embodied pressure intensification device.
Figure 8:
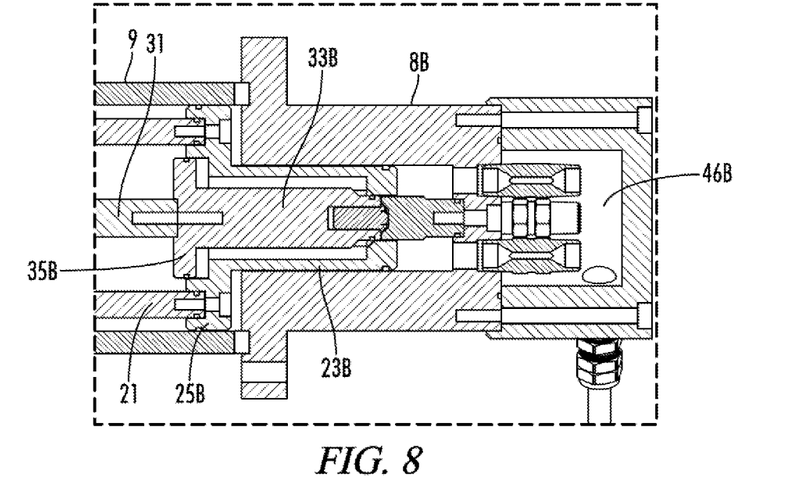
FIG. 8 shows an enlarged cross sectional view of the pressure intensification device of FIG. 7.

However, as shown in FIGS. 7 and 8, since the second outer piston 20B does not encounter the second stop post 43B it is able to continuing moving to the right. The second outer piston 20B can move to the right at least until the seals 50 between the second inner piston 30B and the second outer piston 20B are broken, thereby opening the second channel 15B. The opening of the second channel 15B eliminates the hydraulic ratio advantage, and permits the fluid in second pressurization chamber 42B to exit and normalize in pressure with the fluid in the driving chamber 41.

Figure 9:
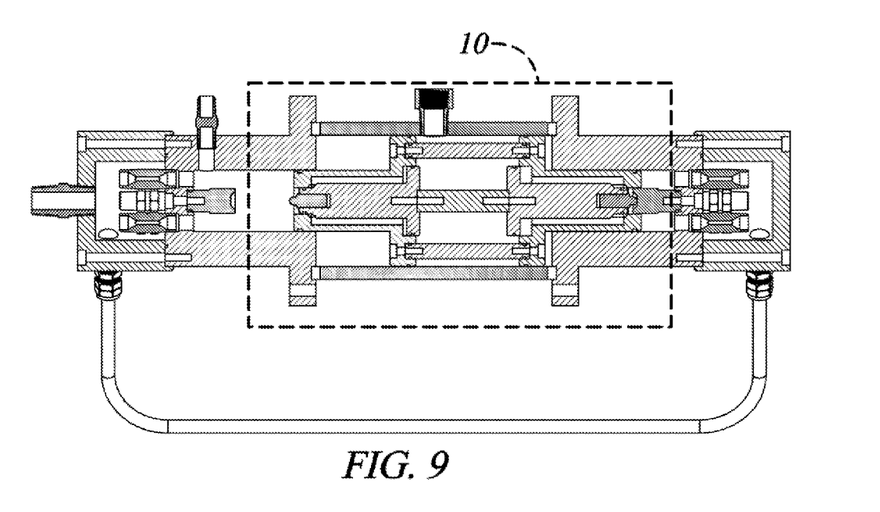
FIG. 9 shows a cross sectional view of the embodied pressure intensification device.
Figure 10:
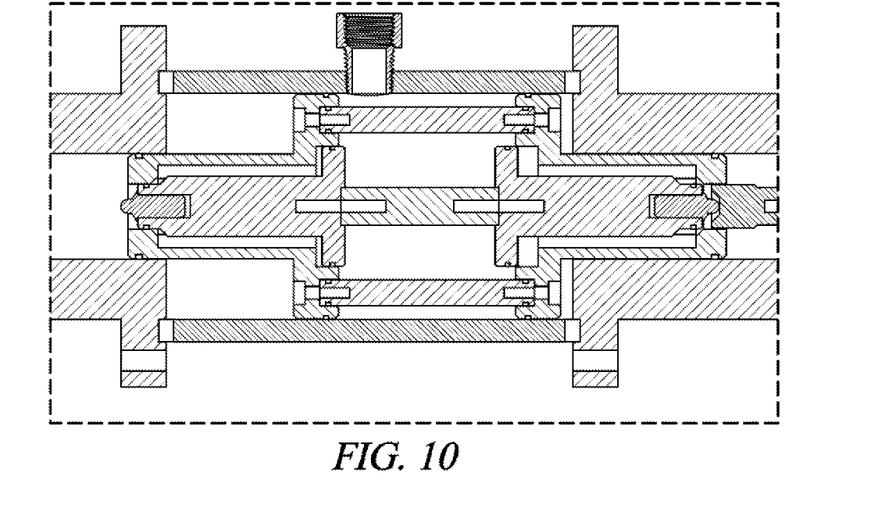
FIG. 10 shows an enlarged cross sectional view of the pressure intensification device of FIG. 9.

As shown in FIGS. 9 and 10, the outflow of the fluid from the second pressurization chamber 42B towards the driving chamber 41 can push the inner element 11 to the left. The inner element 11 can continue being moved to the left by the residual high pressure in the second pressurization chamber 42B until the first inner piston 30A becomes sealed with the first outer piston 20A.

Figure 11:
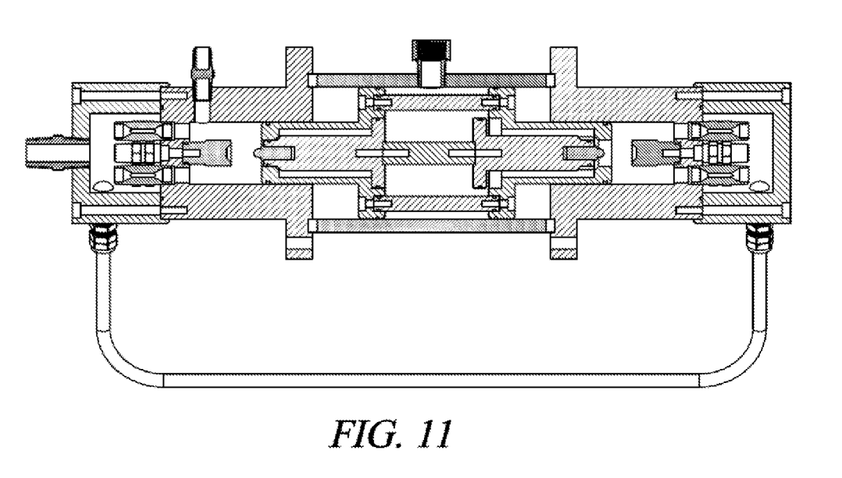
FIG. 11 shows a cross sectional view of the embodied pressure intensification device.

As shown in FIG. 11, once the first inner piston 30A has moved to the left enough to permit one or more seals 50 to form and close the first channel 15A, a hydraulic intensification state is once again created. Fluid at a first pressure in the driving chamber 41 will now start pushing the combined outer and inner elements 11, 13 to the left, compressing water in the first pressurization chamber 42A. The second pressurization chamber 42B is now unsealed, allowing it to be refilled through the second channel 15B.

The inner element 11 and the outer element 13 will continue stroking left until they encounter the first stop post 43A in the first pressurization chamber 42A, whereupon compression to the first pressurization chamber 42A ends and the process switches back to the right stroke mode. This intensification process can continue cycling until either the input fluid source is removed or until the exit flow is stopped. In order to maintain a desired pressure output, the output flow rate can be controlled by the use of a flow restrictor in the output plumbing. In some embodiments a flow restrictor can determine the cycling rate of the device. In other embodiments two or more pressure intensification devices can be connected in series to achieve a desired fluid pressure.

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a piston" includes a plurality of such pistons, and so forth.

Unless otherwise indicated, all numbers used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter. It is also understood that each unit between two particular units are also disclosed. For example, if 10 and 15 are disclosed, then 11, 12, 13, and 14 are also disclosed.

LIST OF NUMBERED ELEMENTS

1—pressure intensification device
2—inlet
3—device outlet
5—loop channel
7—outer shell
8—distal section of outer shell
9—center section of outer shell
11—inner element
13—outer element
15—channel
16—channel inlet
17—channel outlet
20—outer piston
21—outer piston connector
23—outer piston body
25—outer piston head
27—seat
30—inner piston
31—inner piston connector
33—inner piston body
34—protrusion
35—inner piston head
41—driving chamber
42—pressurization chamber
43—stop post
44—pressurization chamber outlet
45—valve
46—exit chamber
47—input valve
50—seal (o-ring)

What is claimed is:
1. A device, comprising:
an outer shell that includes a center section positioned between a first distal section and a second distal section;
a driving chamber defined by the center section;
an inlet in communication with the driving chamber;
an annular outer element housed within the outer shell including a first outer piston that is coupled to and opposed to a second outer piston, each of the outer pistons forming a seal with an interior side of the outer shell and being slideably received by the first and second distal sections;
an inner element housed within the outer element including a first inner piston that is coupled to and opposed to a second inner piston, each of the inner pistons being slideably received by and being configured to form a seal with each of the first and second outer pistons;

a first pressurization chamber within the first distal section that includes a first outlet and a second pressurization chamber within the second distal section that includes a second outlet, the pressurization chambers being defined by interior sides of the first and second distal sections, a distal end of each of the first and second outer pistons, and a distal end of each of the first and second inner pistons; and a first channel communicating between the driving chamber and the first pressurization chamber and a second channel communicating between the driving chamber and the second pressurization chamber.

2. The device of claim 1, further comprising a device outlet in communication with at least one of the first outlet or the second outlet.

3. The device of claim 1, wherein each of the outer pistons include an outer piston head and an outer piston body distally extending from each of the outer piston heads, each of the outer piston heads forming a seal with an interior side of the driving chamber, and each of the outer piston bodies being slideably received by and forming a seal with each of the first and second distal sections.

4. The device of claim 3, wherein a diameter of the outer piston head is greater than a diameter of the outer piston body.

5. The device of claim 3, wherein each of the first and second inner pistons include an inner piston head and an inner piston body distally extending from the inner piston heads, each of the inner piston heads being configured to form a seal with the outer piston heads, and each of the inner piston bodies being slideably received by and being configured to form a seal with each one of the first and second outer pistons.

6. The device of claim 5, wherein the outer piston heads each comprise a seat for engaging each of the inner piston heads.

7. The device of claim 5, wherein a diameter of the inner piston head is greater than a diameter of the inner piston body.

8. The device of claim 1, wherein the first channel is closed at least when the first inner piston is fully received by the first outer piston, and wherein the second channel is closed at least when the second inner piston is fully received by the second outer piston.

9. The device of claim 1, further comprising a first stop post and a second stop post housed within each of the first and second pressurization chambers, the stop posts being configured to limit the range of motion of the inner element with respect to the outer element.

10. The device of claim 9, wherein the first stop post is configured open the first channel when the first outer piston is fully received by the first pressurization chamber, the second stop post is configured open the second channel when the second outer piston is fully received by the second pressurization chamber, or both.

11. The device of claim 1, wherein the outer element and the inner element are configured to slide in a reciprocating manner within the outer shell.

12. The device of claim 1, wherein one or both of the first outlet and the second outlet include a valve.

13. The device of claim 1, further comprising a loop channel in communication with the first outlet and the second outlet.

14. The device of claim 1, wherein one or more of the seals include an o-ring.

15. The device of claim 1, wherein the device is configured to receive a fluid via the inlet at a first pressure and release the fluid via at least one of the first outlet or the second outlet at a second pressure, and wherein the second pressure is greater than the first pressure.

16. The device of claim 1, wherein the device does not comprise an additional power source.

17. The device of claim 1, the first outer piston and the second outer piston are coupled via a fluid permeable structure.

18. The device of claim 17, wherein the fluid permeable structure includes a plurality of bolts coupling the first outer piston to the second outer piston.

19. The device of claim 1, wherein the first channel is positioned between the first inner piston and the first outer piston, or the second channel is positioned between the second inner piston and the second outer piston.

20. The device of claim 1, wherein the first inner piston includes a first protrusion extending from a distal end thereof, or the second inner piston includes a second protrusion extending from a distal end thereof.

21. The device of claim 1, further comprising a first outer sleeve positioned in the first pressurization chamber for receiving the first outer piston, or a second outer sleeve is positioned in the second pressurization chamber for receiving the second outer piston.

22. A device for increasing the pressure of a fluid, comprising:

an outer shell that includes a center section positioned between a first distal section and a second distal section;

a driving chamber defined by the center section;

an inlet in communication with the driving chamber;

an annular outer element housed within the outer shell including a first outer piston that is coupled to a second outer piston, each outer piston including an outer piston head that forms a seal with an interior side of the center section and an outer piston body that extends from each of the outer piston heads, the outer piston bodies being slideably received by and forming a seal with the first and second distal sections;

an inner element housed within the outer element including a first inner piston that is coupled to a second inner piston, each of the inner pistons including an inner piston head that is configured to form a seal with each of the outer piston heads and an inner piston body that extends from each of the inner piston heads, the inner piston bodies being slideably received by and configured to form a seal with the outer piston bodies;

a first pressurization chamber that includes a first outlet and a second pressurization chamber that includes a second outlet, the pressurization chambers being defined by the first and second distal sections, a distal end of each of the first and second outer pistons, and a distal end of each of the first and second inner pistons;

a first channel communicating between the driving chamber and the first pressurization chamber and a second channel communicating between the driving chamber and the second pressurization chamber; and a device outlet in communication with at least one of the first outlet or the second outlet.

23. The device of claim 22, wherein the first and second channels are closed at least when the first and second inner pistons are fully received by the first and second outer pistons.

24. The device of claim 22, further comprising a first stop post and a second stop post housed within each of the first and second pressurization chambers, the stop posts being configured to limit the range of motion of the inner element with respect to the outer element.

25. The device of claim 24, wherein the first stop post is configured open the first channel when the first outer piston is fully received by the first pressurization chamber, and wherein the second stop post is configured open the second channel when the second outer piston is fully received by the second pressurization chamber.

26. The device of claim 22, wherein the outer element and the inner element are configured to slide in a reciprocating manner within the outer shell.

27. The device of claim 22, wherein one or both of the first outlet and the second outlet include a valve.

28. The device of claim 22, further comprising a loop channel in communication with the first outlet and the second outlet.

29. The device of claim 22, wherein one or more of the seals include an o-ring.

30. The device of claim 22, wherein the device is configured to receive a fluid via the inlet at a first pressure and release the fluid via the device outlet at a second pressure, and wherein the second pressure is greater than the first pressure.

31. The device of claim 22, the first outer piston and the second outer piston are coupled via a fluid permeable structure.

32. The device of claim 22, wherein the first channel is positioned between the first inner piston and the first outer piston, and wherein the second channel is positioned between the second inner piston and the second outer piston.

33. The device of claim 22, wherein the first inner piston includes a first protrusion extending from a distal end thereof, and wherein the second inner piston includes a second protrusion extending from a distal end thereof.

34. The device of claim 22, further comprising a first outer sleeve positioned in the first pressurization chamber for receiving the first outer piston, and wherein a second outer sleeve positioned in the second pressurization chamber for receiving the second outer piston.

35. A method, comprising:
providing a device that includes:
an outer shell that includes a center section positioned between a first distal section and a second distal section;
a driving chamber defined by the center section;
an inlet in communication with the driving chamber;
an annular outer element housed within the outer shell including a first outer piston that is coupled to and opposed to a second outer piston, each of the outer pistons forming a seal with an interior side of the outer shell and being slideably received by the first and second distal sections;
an inner element housed within the outer element including a first inner piston that is coupled to and opposed to a second inner piston, each of the inner pistons being slideably received by and being configured to form a seal with the first and second outer pistons;
a first pressurization chamber within the first distal section that includes a first outlet and a second pressurization chamber within the second distal section that includes a second outlet, the pressurization chambers being defined by interior sides of the first and second distal sections, a distal end of the first and second outer pistons, and a distal end of the first and second inner pistons;
a first channel communicating between the driving chamber and the first pressurization chamber and a second channel communicating between the driving chamber and the second pressurization chamber; and
a device outlet in communication with at least one of the first outlet or the second outlet;
providing a fluid at a first pressure to the device inlet; and
releasing the fluid at a second pressure via the device outlet, the second pressure being greater than the first pressure.

36. The method of claim 35, wherein a ratio of the second pressure to the first pressure is about 2 to about 30.

37. The method of claim 35, wherein the first pressure is about 20 psi to about 5,000 psi, and wherein the second pressure is about 50 psi to about 100,000 psi.

38. The method of claim 35, wherein the fluid is water.

39. The method of claim 35, further comprising utilizing the fluid at the second pressure for a cleaning process, a milling process, or a combination thereof.

* * * * *